United States Patent
Halloran et al.

[11] Patent Number: 6,118,014
[45] Date of Patent: Sep. 12, 2000

[54] ORGANOFUNCTIONAL COCYCLIC SILOXANES

[75] Inventors: Daniel Joseph Halloran, Midland; Brett Lee Zimmerman, Birch Run, both of Mich.

[73] Assignee: Dow Corning Corporation, Midland, Mich.

[21] Appl. No.: 09/354,675

[22] Filed: Jul. 16, 1999

[51] Int. Cl.$^7$ ................................ C07F 7/08; C07F 7/10
[52] U.S. Cl. .................... 556/439; 556/425; 556/479; 554/77
[58] Field of Search ................... 556/439, 425, 556/479, 77

[56] References Cited

U.S. PATENT DOCUMENTS

| | | | |
|---|---|---|---|
| 3,299,112 | 1/1967 | Bailey | 260/448 |
| 3,419,593 | 12/1968 | Willing | 260/448 |
| 3,715,334 | 2/1973 | Karstedt | 260/46 |
| 3,814,730 | 6/1974 | Karstedt | 260/46 |
| 3,923,705 | 12/1975 | Smith | 260/2 |
| 5,160,494 | 11/1992 | Krzysik | 512/3 |
| 5,175,325 | 12/1992 | Brown | 556/9 |
| 5,395,955 | 3/1995 | Okawa | 556/449 |
| 5,892,084 | 4/1999 | Janeiro et al. | 556/425 |

FOREIGN PATENT DOCUMENTS 2185984  8/1987  United Kingdom ................... 556/425

*Primary Examiner*—Paul F. Shaver
*Attorney, Agent, or Firm*—James L. De Cesare

[57] ABSTRACT

New compositions of matter are organofunctional cocyclic siloxanes of the formula

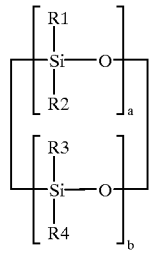

where R1 to R3 are alkyl groups of 1–6 carbon atoms; a and b have a value of 1–10; and R4 is an aminoalkyl group or a carboxyalkyl group. Some representative R4 groups are —$CH_2CH_2CH_2NH_2$, —$CH_2CH_2CH_2NHCH_2CH_2NH_2$, —$CH_2CH(CH_3)CH_2NHCH_2CH_2NH_2$, and —$(CH_2)_{10}COOH$.

4 Claims, No Drawings

ORGANOFUNCTIONAL COCYCLIC SILOXANES

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to new compositions of matter, and more particularly to (i) a dialkyl, alkyl aminoalkyl cocyclic siloxane, preferably a dimethyl, methyl aminoalkyl cocyclic siloxane, and (ii) a dialkyl alkyl carboxyalkyl cocyclic siloxane, preferably a dimethyl, methyl carboxyalkyl cocyclic siloxane. These compositions are prepared by hydrosilation and are useful as oligomers in the preparation of other siloxane polymers.

BACKGROUND OF THE INVENTION

While cocyclic siloxanes are generally known in the prior art, the organofunctional cocyclic siloxanes of the present invention are not believed to be described in the literature.

For example, U.S. Pat. No. 3,299,112 (Jan. 17, 1967), relates to certain dimethyl methyl polyether cocyclic siloxanes; U.S. Pat. No. 5,160,494 (Nov. 3, 1992) relates to certain dimethyl methyl higher alkylmethyl cocyclic siloxanes; and U.S. Pat. No. 5,395,955 (Mar. 7, 1995) relates to certain dimethyl methyl carbinol cocyclic siloxanes. In addition, U.S. Pat. Nos. 5,160,494 and 5,395,955 also describe certain dimethyl methyl hydrogen cocyclic siloxanes. However, none of these patents describe either the (i) dialkyl, alkyl aminoalkyl cocyclic siloxane, or (ii) the dialkyl, alkyl carboxyalkyl cocyclic siloxane, of this invention.

BRIEF SUMMARY OF THE INVENTION

The invention relates to a composition of matter, which in one embodiment, is a cocyclic siloxane having the formula

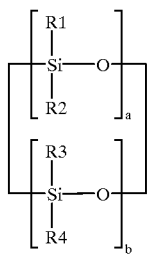

where R1 to R3 are each an alkyl group containing 1–6 carbon atoms; a and b are each a positive integer having a value of 1–10; and R4 is an aminoalkyl group having the formula

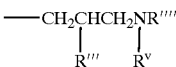

where R''' and R'''' are each hydrogen or an alkyl group containing 1–4 carbon atoms, $R^v$ is hydrogen or a group having the formula

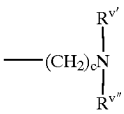

where c is a positive integer having a value of 2 or 3, and $R^{v'}$ and $R^{v''}$ are hydrogen or an alkyl group containing 1–4 carbon atoms.

Alkyl groups represented by R1, R2, R3, R''', R'''', $R^v$, and $R^{v''}$ include methyl, ethyl, propyl, isopropyl, butyl, and isobutyl.

In this first embodiment, the R4 aminoalkyl groups most preferred are —CH$_2$CH$_2$CH$_2$NH$_2$, —CH$_2$CH$_2$CH$_2$NHCH$_2$CH$_2$NH$_2$, and —CH$_2$CH(CH$_3$)CH$_2$NHCH$_2$CH$_2$NH$_2$.

In another embodiment, the invention relates to a composition of matter which is a cocyclic siloxane having the formula

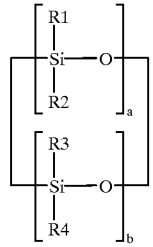

where R1 to R3 are each an alkyl group containing 1–6 carbon atoms; R4 is a carboxyalkyl or carboxyalkyl derivative group having the formula —(CHR5)$_n$COOR6 where R5 is hydrogen or an alkyl group containing 1–6 carbon atoms; R6 is hydrogen, an alkyl group containing 1–6 carbon atoms, or a trialkylsilyl group —Si(R7)$_3$ in which R7 is an alkyl group containing 1–6 carbon atoms; a and b are each a positive integer having a value of 1–10; and n is a positive integer having a value of 3–20.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

Hydrosilation is a known reaction involving the addition of a silicon hydride to an unsaturated hydrocarbon to form a silicon-carbon bond. It is used commercially to synthesize organofunctional silicon monomers, to crosslink silicone polymers, and to connect a silicone to an organic polymer block to form a copolymer. One example is the hydrosilation of an alpha-olefin with a methylhydrogen siloxane, according to the reaction:

≡SiH+CH$_2$=CH—R+catalyst→≡SiCH$_2$CH$_2$—R.

When used for crosslinking, such platinum catalyzed hydrosilation reactions typically involve reaction between a low molecular weight polysiloxane containing several ≡Si—H groups and a high molecular weight polysiloxane containing several ≡Si-vinyl groups, or vice versa.

Generally, stoichiometric amounts of the ≡SiH containing reactant, and the reactant containing unsaturation, should be employed in the process. It may be necessary, however, to use an excess of the reactant containing unsaturation to totally consume the ≡SiH in the siloxane product.

The maximum amount of platinum catalyst employed is determined by economical considerations, and the minimum amount is determined by the type and purity of the reactants employed. Generally, very low concentrations of platinum catalyst, such as $1 \times 10^{-10}$ moles catalyst per equivalent of the reactant containing unsaturation, may be used when the reactants are extremely pure. However, it is possible to use about $1 \times 10^{-8}$ moles catalyst per equivalent weight of reactant containing unsaturation, and even $1 \times 10^{-7}$ to $1 \times 10^{-3}$ moles platinum catalyst per equivalent weight of reactant containing unsaturation.

Moles of platinum catalyst are measured in terms of one mole providing one unit atom (e.g. one gram atom) of platinum. An equivalent weight of reactant containing unsaturation is the amount of reactant furnishing one unit weight of ethylenic unsaturation (i.e. equivalent to one unit weight of ≡SiH), regardless of what other reactive or potentially reactive substitutents may be present. Thus, an equivalent weight of ethylene is its molecular weight.

According to this invention, the platinum catalyst should be present in an amount sufficient to provide from about 100 to about 200 parts by weight of platinum per one million parts by weight of the reaction mixture, i.e., 100–200 ppm.

Conventional wisdom suggest that hydrosilation reactions involving the addition of a silicon hydride to an unsaturated hydrocarbon such as an unsaturated amine to form a silicon-carbon bond, should not be feasible, due to platinum contamination by polar groups such as the amine. It has been found unexpectedly, however, that according to this invention, these reactions can be made to proceed readily when greater than about 100 ppm platinum is used.

The reaction temperature can vary, and optimum temperatures depend upon the concentration of platinum catalyst and the nature of the reactants. The reaction can be initiated at a temperature below room temperature, i.e., 0° C. to −10° C., and is exothermic once it begins. The temperature should be one at which the reactants are in a liquid or gaseous state. The maximum temperature is determined by the stability of the reactants.

Ordinarily, it is best to keep the reaction temperature below about 300° C. Best results with most reactants are obtained by initiating the reaction at about 80–180° C., and maintaining the reaction within reasonable limits of this range. The exothermic nature of the reaction may push the temperature up to 200–250° C. for a short time, however.

The optimum reaction time is a variable depending upon the reactants, reaction temperature, and platinum catalyst concentration. Ordinarily, there is no benefit in extending the contact time of the reactants beyond 16 or 17 hours, but likewise there is usually no harm, unless an extremely elevated temperature is employed. With many reactants, a practical quantitative yield of product can be obtained in 30 minutes or less.

The reaction can be carried out at atmospheric, sub-atmospheric, or super-atmospheric pressure. Here again, the choice of conditions is largely a matter of logic, based upon the nature of the reactants, and the equipment available. Non-volatile reactants are especially adaptable to being heated at atmospheric pressure with or without a reflux arrangement. Reactants which are gaseous at ordinary temperatures are preferably reacted at substantially constant volume under autogenous or induced pressure. The best results are obtained by maintaining all reactants in the liquid phase.

As noted above, hydrosilation requires a catalyst to effect the reaction between the ≡SiH containing reactant and the reactant containing unsaturation. Suitable catalysts are Group VIII transition metals. Some examples of metal catalysts which can be used are a platinum catalyst in the form of the reaction product of chloroplatinic acid and an organosilicon compound containing terminal aliphatic unsaturation, as described in U.S. Pat. No. 3,419,593 (Dec. 31, 1968). Another suitable catalyst is Karstedt's catalyst as described in his U.S. Pat. No. 3,715,334 (Feb. 6, 1973) and U.S. Pat. No. 3,814,730 (Jun. 4, 1974), which is a platinum-vinylsiloxane substantially free of chemically combined halogen. Several types of catalysts, including deposited platinum type catalysts as well as complexed platinum type catalysts, are described in detail in U.S. Pat. No. 3,923,705 (Dec. 2, 1975). Yet another suitable catalyst is a platinum-organosiloxane complex prepared by reacting a platinous halide with an organosiloxane having 2–4 silicon bonded organic groups containing terminal olefinic unsaturation, in the presence of a polar organic liquid which is a partial solvent for the platinous halide, as described in U.S. Pat. No. 5,175,325 (Dec. 29, 1992). Still another suitable hydrosilation catalyst is platinum supported on active carbon particles of a diameter of 1–2 mm, in which the amount of platinum supported on the active carbon varies from 0.1–5 percent by weight, based on the weight of the active carbon.

Among such catalysts, the catalyst most preferred according to this invention is the neutralized complex of platinous chloride and divinyltetramethyldisiloxane described in U.S. Pat. No. 5,175,325.

The ≡SiH containing reactant according to the present invention is a cocyclic siloxane having the formula

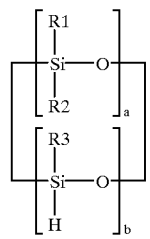

where R1 to R3 are each an alkyl group containing 1–6 carbon atoms, and a and b are each a positive integer having a value of 1–10. Alkyl groups generally representative of R1, R2, and R3 include methyl, ethyl, propyl, isopropyl, butyl, isobutyl, pentyl, and hexyl.

Such ≡SiH containing cocyclic siloxanes and methods for their preparation are known in the art, and reference may be had, for example, to U.S. Pat. No. 5,160,494 (Nov. 3, 1992), and U.S. Pat. No. 5,395,955 (Mar. 7, 1995).

The ≡SiH containing reactant most preferred according to the present invention is a cocyclic siloxane having the formula

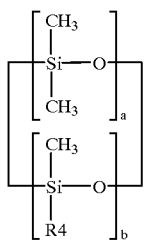

where R4 has the same meaning as defined above, a has an average value of 4, and b has an average value of one.

The reactant containing unsaturation which is used to prepare the dialkyl, alkyl methyl aminoalkyl cocyclic siloxane by hydrosilation is an unsaturated amine having the formula

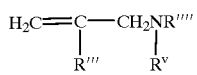

where R''' and R'''' are hydrogen or an alkyl group containing 1–4 carbon atoms; $R^v$ is hydrogen or a group having the formula

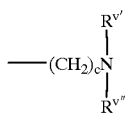

in which c is a positive integer having a value of 2 or 3, and $R^{v'}$ and $R^{v''}$ are hydrogen or an alkyl group containing 1–4 carbon atoms.

Some representative unsaturated amines most preferred for use herein are allyl amine $H_2C$=$CHCH_2NH_2$, the compound $H_2C$=$CHCH_2NHCH_2CH_2NH_2$, or the compound $H_2C$=$C(CH_3)CH_2NHCH_2CH_2NH_2$.

The reactant containing unsaturation which is used to prepare the dialkyl, alkyl carboxyalkyl cocyclic siloxane by hydrosilation is an alkenoic acid, preferably an alkenoic acid which has a melting point of about 40° C. or less. Some examples of suitable alkenoic acids which can be used are 3-butenoic acid (vinylacetic acid) $H_2C$=$CHCH_2COOH$, 4-pentenoic acid (allylacetic acid) $H_2C$=$CH(CH_2)_2COOH$, trans-2-pentenoic acid $C_2H_5CH$=$CHCOOH$, trans-3-hexenoic acid $C_2H_5CH$=$CHCH_2COOH$, 6-heptenoic acid $H_2C$=$CH(CH_2)_4COOH$, and 10-undecenoic acid (undecylenic acid) $H_2C$=$CH(CH_2)_8COOH$.

If desired, the alkenoic acid can be used in the hydrosilation reaction in an esterified form. Alternatively, and optionally, the alkenoic acid can be protected/silylated. Thus, it may be desirable to protect the hydroxyl group —OH of the alkenoic acid in order to prevent undesired reactions during reactions on other parts of the molecule in the hydrosilation reaction. Following hydrosilation, the protecting group can be removed.

A number of reagents have been developed for protecting and for removing such groups. For example, trimethylsilyl protecting groups, i.e., $(CH_3)_3Si$—, can be provided by reaction of the alkenoic acid with a silylating reagent such as hexamethyldisilazane, i.e., $(CH_3)_3SiNHSi(CH_3)_3$, or trimethylchlorosilane, i.e., $(CH_3)_3SiCl$.

Following the main hydrosilation reaction, the trimethylsilyl protecting group can be removed by contacting the product of hydrosilation with a desilylating reagent such as an alcohol, typically, an alcohol such as methanol, ethanol, or isopropanol. These protecting/deprotecting steps may require the presence of a solvent, among which can be used aromatic hydrocarbons such as toluene, benzene, and xylene, or ethers such as diethyl ether and tetrahydrofuran. The solvent and any reaction product formed during these optional protecting/deprotecting steps can be removed in order to obtain the desired product.

In view of the above, the reactant containing unsaturation can be best described as an alkenoic acid or an alkenoic acid derivative having the general formula $(H2C)_m$=$CR5(CR5_2)_nCOOR6$ where R5 is hydrogen or an alkyl group containing 1–6 carbon atoms; R6 is hydrogen, an alkyl group containing 1–6 carbon atoms, or a trialkylsilyl group —$Si(R7)_3$ where R7 is an alkyl group containing 1–6 carbon atoms; m is a positive integer having a value of 1–3; and n is a positive integer having a value of 1–20.

EXAMPLES

The following examples are set forth in order to illustrate this invention in more detail. In these examples, the catalyst was a neutralized complex of platinous chloride and divinyltetramethyldisiloxane generally as described in U.S. Pat. No. 5,175,325. The ≡SiH containing reactant was a cocyclic siloxane having the formula

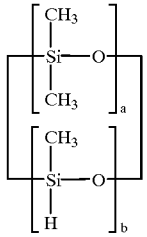

where a had an average value of 4 and b had an average value of one. The reactant containing unsaturation was allylamine.

Example 1–3

General Procedure

Into a reaction flask was placed the ≡SiH containing cocyclic siloxane and the platinum catalyst. The reaction flask was purged with nitrogen, and the allylamine was added dropwise to the flask to control the evolution of heat. After the addition, the reaction flask was heated to a temperature in the range of about 80–100° C. Heating was continued, and the temperature of the reaction flask was maintained for about 6–24 hours. The reaction flask was cooled to room temperature, and the level of any unreacted ≡SiH was measured using infrared spectroscopy. This determination was followed by analysis of the product of the hydrosilation reaction by means of gas chromatography and mass spectrometry. The various parameters of these examples are set forth in Table 1.

TABLE 1

Examples 1 to 3

| Parameter | Example 1 | Example 2 | Example 3 |
|---|---|---|---|
| Amount of ≡SiH Cocyclic Siloxane (gram) | 84.6 | 84.6 | 84.6 |
| Amount of Allylamine (gram) | 85.0 | 17.1 | 17.1 |
| Molar Ratio ≡SiH Cocyclic Siloxane/Allylamine | 1:5 | 1:1 | 1:1 |
| Parts per million Platinum | 200 | 200 | 200 |
| Reaction Time (hours) | 24 | 6 | 6 |
| Reaction Temperature (° C.) | 100 | 80 | 80 |
| Results: Gas Chromatography/Mass Spectrometry | $D^{R4}D_3$ | $D^{R4}D_3$ and $D^{R4}D_4$ | $D^{R4}D_3$ and $D^{R4}D_4$ |
| Parts per million ≡SiH via Infrared Spectroscopy | 0 | 0 | 2.3 |

The products prepared by hydrosilation in Examples 1–3, i.e., $D^{R4}D_3$ and $D^{R4}D_4$, have the structure shown below wherein R4 was the group —$CH_2CH_2CH_2NH_2$, b had a value of one, and a had values of 3 and 4, respectively.

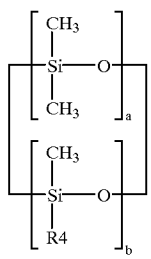

Example 4A

Silylation/Protection of Undecylenic Acid

Into a reaction flask was placed 276.4 gram of undecylenic acid and 196.8 gram of toluene which was used as a solvent. The reaction flask was purged with nitrogen, and then 120.8 gram of hexamethyldisilazane which was used as the silylation reagent, was added dropwise to the flask. The reaction flask was heated to a temperature of about 110° C. Heating was continued, and the temperature of the reaction flask was maintained for about 3 hours. The toluene solvent was removed by reducing the pressure in the reaction flask. The reaction flask containing the silylated alkenoic acid was cooled to room temperature, and the extent of the reaction to insure completion was determined by infrared spectroscopy. Analysis by gas chromatography, $C_{13}$ nuclear magnetic resonance (NMR), and mass spectrometry confirmed that the product was trimethylsilylundecylate, i.e., $H_2C$=CH$(CH_2)_8COOSi(CH_3)_3$.

Example 4B

General Procedure

Into a reaction flask was placed 48.5 gram of trimethylsilylundecylate prepared in Example 4A and 50 parts per million of platinum catalyst. The reaction flask was purged with nitrogen, and then 85 gram of the ≡SiH containing cocyclic siloxane was added dropwise to the flask. The molar ratio of ≡SiH containing cocyclic siloxane to trimethylsilylundecylate was 1:1. The reaction flask was heated to a temperature of about 110° C. Heating was continued, and the temperature of the reaction flask was maintained for about 3 hours. The reaction flask was cooled to room temperature. The level of unreacted ≡SiH was measured using infrared spectroscopy, and determined to be zero parts per million residual ≡SiH. Analysis of the product by means of gas chromatography and mass spectrometry confirmed that a silylated dimethyl methyl carboxyfunctional cocyclic siloxane had been prepared.

Example 4C

Preparation of Carboxyalkyl Cocyclic Siloxane/Removal of Protecting Group

Into a reaction flask were placed 90 gram of the silylated dimethyl methyl carboxyfunctional cocyclic siloxane prepared in Example 4B, and 30 gram of methanol which was used as the desilylating reagent. The reaction flask was purged with nitrogen, and then the reaction flask was heated to a temperature of about 110° C. Heating was continued, and the temperature of the reaction flask was maintained for about 3 hours. The methanol desilylating reagent and by-product were removed by reducing the pressure in the heated reaction flask. The by-product was trimethylmethoxysilane, i.e., $(CH_3O)Si(CH_3)_3$, which was formed as a result of the reaction between the desilylating reagent and the silylated dimethyl methyl carboxyfunctional cocyclic siloxane. The reaction flask containing the desired product, i.e., the desilylated dimethyl methyl carboxyalkyl cocyclic siloxane, was cooled to room temperature. Analysis of the product by means of gas chromatography and mass spectrometry confirmed that it consisted of a mixture of $D^{R4}D_4$ and $D^{R4}D_5$, having the structure shown below, where R4 was the group —$(CH_2)_{10}COOH$, b had a value of one, and a had values of 4 and 5, respectively.

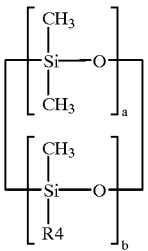

Other variations may be made in compounds, compositions, and methods described without departing from the essential features of the invention. The embodiments illustrated are exemplary only and not intended as limitations on their scope except as defined in the claims.

What is claimed is:

1. A composition of matter comprising a cocyclic siloxane having the formula

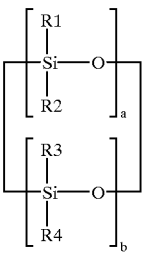

where R1 to R3 are each an alkyl group containing 1–6 carbon atoms; R4 is a carboxyalkyl or carboxyalkyl derivative group having the formula —(CHR5)$_n$COOR6 where R5 is hydrogen or an alkyl group containing 1–6 carbon atoms; R6 is hydrogen, an alkyl group containing 1–6 carbon atoms, or a trialkylsilyl group —Si(R7)$_3$ where R7 is an alkyl group containing 1–6 carbon atoms; a and b are each a positive integer having a value of 1–10; and n is a positive integer having a value of 3–20.

2. A composition according to claim 1 in which R1 to R3 are each the methyl group.

3. A composition according to claim 1 in which R4 is the carboxyalkyl group —(CH$_2$)$_{10}$COOH.

4. In a hydrosilation process in which an ≡SiH containing reactant is contacted with a reactant containing unsaturation in the presence of a Group VIII transition metal catalyst, the improvement comprising using as the ≡SiH containing reactant, a cocyclic siloxane having the formula

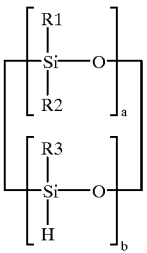

where R1 to R3 are each an alkyl group containing 1–6 carbon atoms, and a and b are each positive integers having a value of 1–10; the reactant containing unsaturation being an alkenoic acid or an alkenoic acid derivative having the formula (H$_2$C)$_m$=CR5(CR5$_2$)$_n$COOR6 where R5 is hydrogen or an alkyl group containing 1–6 carbon atoms; R6 is hydrogen, an alkyl group containing 1–6 carbon atoms, or a trialkylsilyl group —Si(R7)$_3$ where R7 is an alkyl group containing 1–6 carbon atoms; m is a positive integer having a value of 1–3; and n is a positive integer having a value of 1–20.

* * * * *